(12) United States Patent
Wolleschensky (10) Patent No.: US 6,703,621 B2
(45) Date of Patent: Mar. 9, 2004

(54) METHOD FOR THE OPTICAL ACQUISITION OF CHARACTERISTIC SIZES OF AN ILLUMINATED SAMPLE

(75) Inventor: Ralf Wolleschensky, Schoeten (DE)

(73) Assignee: Carl Zeiss Jena GmbH, Jena (DE)

( * ) Notice: Subject to any disclaimer, the term of this patent is extended or adjusted under 35 U.S.C. 154(b) by 0 days.

(21) Appl. No.: 10/051,205

(22) Filed: Jan. 16, 2002

(65) Prior Publication Data

US 2003/0071227 A1 Apr. 17, 2003

(30) Foreign Application Priority Data

Oct. 16, 2001 (DE) .......................... 101 51 216

(51) Int. Cl.[7] .............................................. G01N 21/64
(52) U.S. Cl. ................... 250/459.1; 250/458.1; 356/317; 356/326
(58) Field of Search .................. 250/458.1, 459.1; 356/317, 318, 326, 328

(56) References Cited

U.S. PATENT DOCUMENTS

| | | | | |
|---|---|---|---|---|
| 5,114,236 A | * | 5/1992 | Matsugu et al. ............ 356/401 |
| 5,120,132 A | * | 6/1992 | Spies et al. .................. 356/499 |
| 5,122,660 A | * | 6/1992 | Yoshii et al. ............ 250/237 G |
| 5,459,323 A | * | 10/1995 | Morgan ..................... 250/458.1 |
| 5,673,144 A | * | 9/1997 | Chastang et al. ........... 359/385 |
| 5,742,389 A | * | 4/1998 | Zavislan et al. ............ 356/326 |
| 6,053,613 A | * | 4/2000 | Wei et al. .................... 351/205 |
| 6,097,034 A | * | 8/2000 | Weckstrom et al. ..... 250/495.1 |
| 6,134,003 A | * | 10/2000 | Tearney et al. ............. 356/450 |
| 6,151,185 A | * | 11/2000 | Ishizuka et al. ......... 360/78.04 |
| 6,229,635 B1 | * | 5/2001 | Wulf ........................... 359/196 |
| 6,392,748 B1 | * | 5/2002 | Fateley ....................... 356/330 |
| 6,486,458 B1 | * | 11/2002 | Schoeppe et al. ........... 250/205 |
| 6,496,307 B2 | * | 12/2002 | Engelhardt et al. ......... 359/389 |

* cited by examiner

*Primary Examiner*—Diego Gutierrez
*Assistant Examiner*—Yaritza Guadalupe
(74) *Attorney, Agent, or Firm*—Reed Smith LLP

(57) ABSTRACT

A method for the optical acquisition of characteristic quantities of an illuminated specimen, wherein a signal that is backscattered, reflected and/or fluoresced and/or transmitted from the specimen comprises the steps of detecting the signal by a spatially resolving detector in a plurality of channels in that the radiation coming from the specimen is imaged on the detector so as to be spectrally split and combining detection channels so that the quantity of measurements that are read out and further processed is less than the number of detection channels.

12 Claims, 7 Drawing Sheets a.)

METHOD FOR THE OPTICAL ACQUISITION OF CHARACTERISTIC SIZES OF AN ILLUMINATED SAMPLE

CROSS-REFERENCE TO RELATED APPLICATIONS

This application claims priority of German Application No. 101 51 942.7, filed Oct. 16, 2001, the complete disclosure of which is hereby incorporated by reference.

BACKGROUND OF THE INVENTION a) Field of the Invention

The invention is directed to a method and an arrangement in fluorescence microscopy, particularly laser scanning microscopy, fluorescence correlation spectroscopy, and nearfield scanning microscopy, for the examination of predominantly biological specimens, preparations and associated components. This includes methods for screening active ingredients based on fluorescence detection (high throughput screening) and flow cytometers. The transition from the detection of a few broad-spectrum dye bands to the simultaneous acquisition of whole spectra opens up new possibilities for the identification, separation and correlation of mostly analytic or functional specimen characteristics to spatial partial structures or dynamic processes. Therefore, simultaneous examination of specimens with multiple fluorophores with overlapping fluorescence spectra are even possible in three-dimensional or spatial structures of thick specimens. The spectral resolution of the detection unit is increased by means of the arrangement.

b) Description of the Related Art

A typical area of application of light microscopy for examining biological preparations is fluorescence microscopy (Pawley, "Handbook of Biological Confocal Microscopy"; Plenum Press 1995). In this case, determined dyes are used for specific labeling of cell parts.

Figure 1:
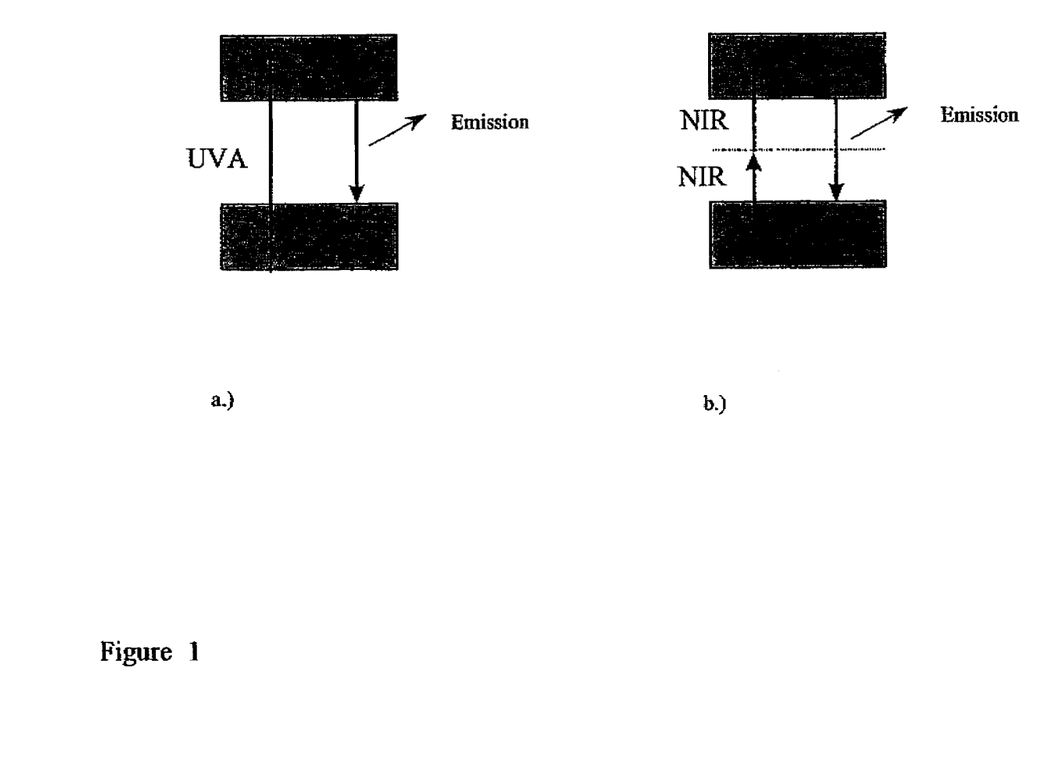
FIG. 1a illustrates single photon absorption in a schematic fashion.
FIG. 1b illustrates multiphoton absorption in a schematic fashion.

The irradiated photons having a determined energy excite the dye molecules, through the absorption of a photon, from the ground state to an excited state. This excitation is usually referred to as single-photon absorption (FIG. 1a). The dye molecules excited in this way can return to the ground state in various ways. In fluorescence microscopy, the most important transition as by emission of a fluorescence photon. Because of the Stokes shift, there is generally a red shift in the wavelength of the emitted photon in comparison to the excitation radiation; that is, it has a greater wavelength. Stokes shift makes it possible to separate the fluorescence radiation from the excitation radiation.

The fluorescent light is split off from the excitation radiation by suitable dichroic beam splitters in combination with blocking filters and is observed separately. This makes it possible to show individual cell parts that are dyed with different dyes. In principle, however, several parts of a preparation can also be dyed simultaneously with different dyes which bind in a specific manner (multiple fluorescence). Special dichroic beam splitters are used again to distinguish the fluorescence signals emitted by the individual dyes.

In addition to excitation of dye molecules with a high-energy photon (single-photon absorption), excitation with a plurality of lower-energy photons is also possible (FIG. 1b). The sum of energies of the single photons corresponds approximately to a multiple of the high-energy photon. This type of excitation of dyes is known as multiphoton absorption (Corle, Kino, "Confocal Scanning, Optical Microscopy and Related Imaging Systems"; Academic Press 1996). However, the dye emission is not influenced by this type of excitation, i.e., the emission spectrum undergoes a negative Stokes shift in multiphoton absorption; that is, it has a smaller wavelength compared to the excitation radiation. The separation of the excitation radiation from the emission radiation is carried out in the same way as in single-photon excitation.

Figure 2:
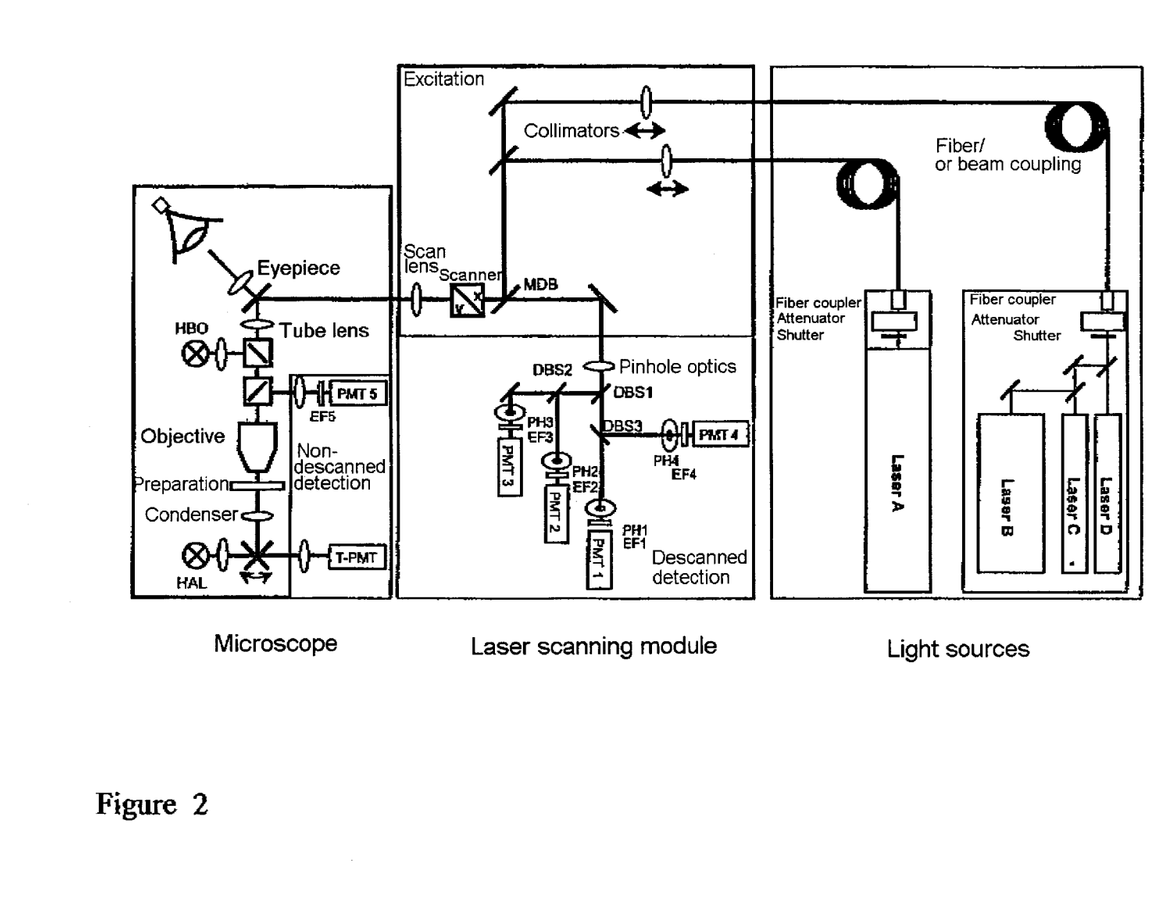
FIG. 2 schematically illustrates a confocal laser scanning microscope (LSM)

The prior art will be explained more fully in the following by way of example with reference to a confocal laser scanning microscope (LSM) (FIG. 2).

An LSM is essentially composed of four modules: light source, scan module, detection unit and microscope. These modules are described more fully in the following. In addition, reference is had to DE19702753A1.

Lasers with different wavelengths are used in an LSM for specific excitation of different dyes in a preparation. The choice of excitation wavelength is governed by the absorption characteristics of the dyes to be examined. The excitation radiation is generated in the light source module. Various lasers (argon, argon/krypton, Ti:Sa lasers) are used for this purpose. Further, the selection of wavelengths and the adjustment of the intensity of the required excitation wavelength is carried out in the light source module, e.g., using an acousto-optic crystal. The laser radiation subsequently reaches the scan module via a fiber or a suitable mirror arrangement.

The laser radiation generated in the light source is focused in the preparation in a diffraction-limited manner by means of the objective (2) via the scanner, scan optics and tube lens. The focus scans the specimen in a point raster in x-y direction. The pixel dwell times when scanning over the specimen are mostly in the range of less than one microsecond to several seconds.

In confocal detection (descanned detection) of fluorescent light, the light emitted from the focal plane (specimen) and from the planes located above and below the latter reaches a dichroic beam splitter (MDB) via the scanner. This dichroic beam splitter separates the fluorescent light from the excitation light. The fluorescent light is subsequently focused on a diaphragm (confocal diaphragm/pinhole) located precisely in a plane conjugate to the focal plane. In this way, fluorescent light components outside of the focus are suppressed. The optical resolution of the microscope can be adjusted by varying the size of the diaphragm. Another dichroic blocking filter (EF) which again suppresses the excitation radiation is located behind the diaphragm. After passing the blocking filter, the fluorescent light is measured by means of a point detector (PMT).

When using multiphoton absorption, the excitation of the dye fluorescence is carried out in a small volume in which the excitation intensity is particularly high. This area is only negligibly larger than the detected area when using a confocal arrangement. Accordingly, a confocal diaphragm can be dispensed with and detection can be carried out directly following the objective (nondescanned detection).

In another arrangement for detecting a dye fluorescence excited by multiphoton absorption, descanned detection is carried out again, but this time the pupil of the objective is imaged in the detection unit (nonconfocal descanned detection).

From a three-dimensionally illuminated image, only the plane (optical section) located in the focal plane of the objective is reproduced by the two detection arrangements in connection with corresponding single-photon absorption or multiphoton absorption. By recording or plotting a plurality of optical sections in the x-y plane at different depths z of the specimen, a three-dimensional image of the specimen can be generated subsequently in computer-assisted manner.

Accordingly, the LSM is suitable for examination of thick preparations. The excitation wavelengths are determined by the utilized dye with its specific absorption characteristics. Dichroic filters adapted to the emission characteristics of the dye ensure that only the fluorescent light emitted by the respective dye will be measured by the point detector.

Figure 3:
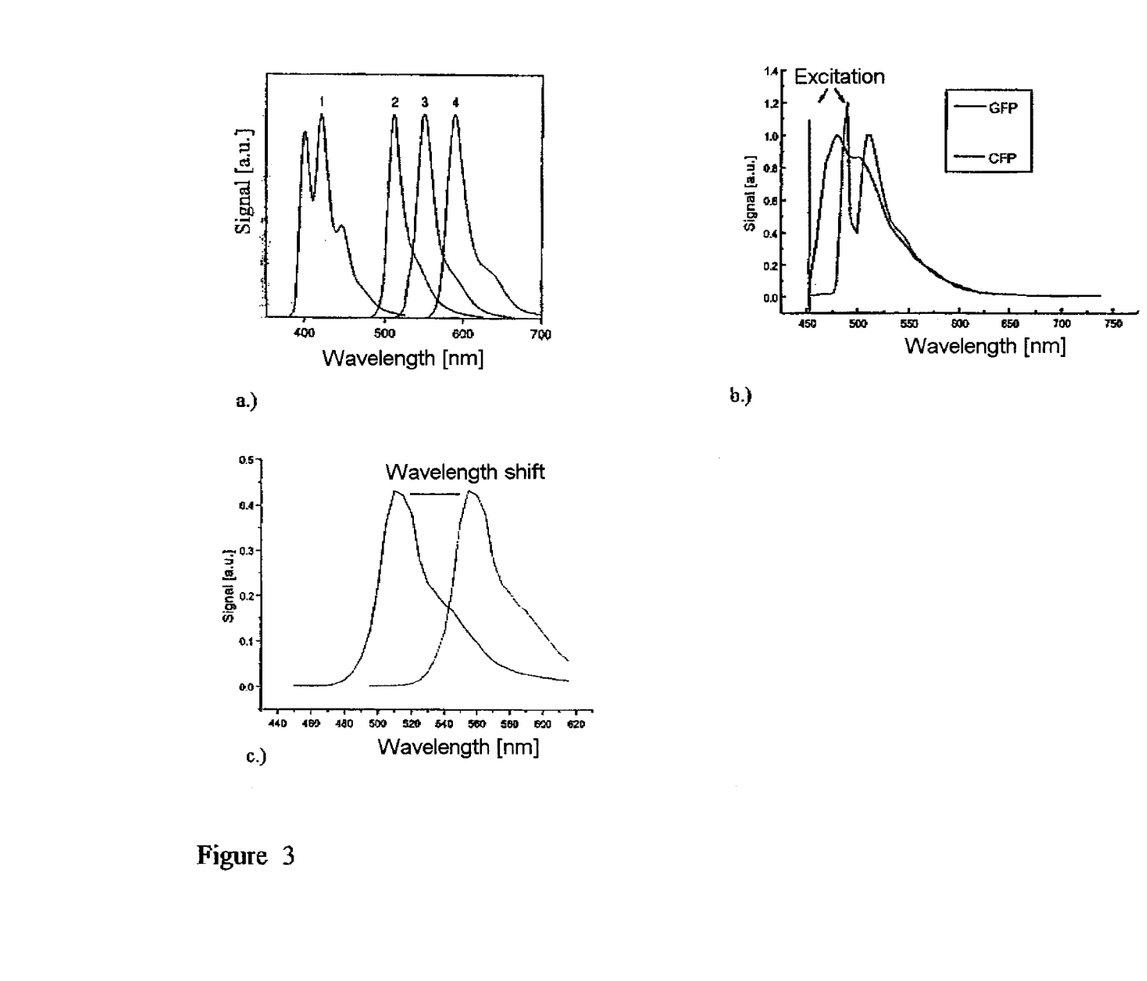
FIG. 3a shows in graphical form how individual dyes can be detected separately based on different absorption characteristics or emission characteristics.
FIG. 3b shows high resolution detection of the dye fluorescence.

Currently, in biomedical applications, a number of different cell regions are labeled simultaneously by different dyes (multifluorescence). In the prior art, the individual dyes can be detected separately based on different absorption characteristics or emission characteristics (spectra) (FIG. 3a). For example, emission signals are plotted over wavelength for different dyes (1–4). For separate detection, an additional splitting of the fluorescent light of a plurality of dyes is carried out with the secondary beam splitters (DBS) and a separate detection of the individual dye emissions is carried out in various point detectors (PMT x). With the arrangement described above, it is impossible for the user to flexibly adapt detection and excitation to corresponding new dye characteristics. Instead, new dichroic beam splitters and blocking filters must be created for every (new) dye.

In a known arrangement, the fluorescent light is split spectrally by means of a prism. The method differs from the above-described arrangement with dichroic filters only in that the characteristic of the utilized filter is adjustable. However, it is still preferable to record the emission band of a dye by point detector.

Fast local measurement of the emission spectrum is possible only conditionally with the two arrangements, since the adjustment of the emission range relies on mechanical movements of the dichroic filter and diaphragms and the maximum spectral resolution is therefore limited to about 5 nm. A high spectral resolution is needed, for example, when the emission spectra overlap as is shown in FIG. 3b. FIG. 3b shows behavior of this kind in the two naturally occurring dyes CFP and GFP. These dyes are particularly suited to examination of living preparations because they have no toxic effect on the specimens to be examined.

When the position of the emission spectrum of the utilized dyes is unknown or when a shift occurs in the emission spectrum depending on environment (FIG. 3c), high-resolution detection of the dye fluorescence is necessary. The wavelength shift can amount to several times 10 nm. Spectrometers are also currently used in combination with an LSM to measure the emission spectrum in the specimen. In so doing, a conventional, usually high-resolution, spectrometer is used instead of a point detector (Patent: Dixon, et al. U.S. Pat. No. 5,192,980). However, these spectrometers can record an emission spectrum only point by point or as an average over a region. Accordingly, this is a kind of spectroscopy. In addition, the usually weak fluorescence signal of the specimen is distributed to a large quantity of individual channels in the spectrometer (usually 512 or 1024 individual channels) or a narrow fluorescence band is detected corresponding to the spectral resolution. Therefore, the signal per individual channel is extremely small and in some cases is not detectable.

OBJECT AND SUMMARY OF THE INVENTION

Therefore, it is the primary object of the invention to provide a novel method for efficient, spectrally resolved detection of fluorescent dyes with a line detector. In the optical arrangements described above, the spectral resolution is determined by the quantity of individual channels. When not all of the individual channels of the detector can be read out simultaneously, a sequential readout of the individual channels is carried out according to the prior art by multiplexing. The multiplexing can be carried out during the pixel dwell time during the scanning of a specimen. This has the disadvantage that the integration time per individual channel during which a signal can be detected is reduced by the quantity of multiplex positions. In addition, when broad fluorescence spectra are measured, the signal is lost in the individual channels that are not read out. In another multiplexing method, the signals of the individual channels can be buffered. The individual storages are then read out one after the other. However, no new data can be recorded during the readout time. Therefore, the readout speed of the line detector would be reduced in this type of multiplexing. Therefore, the method and arrangement according to the invention has the following objectives:

1. The entire spectrally resolved signal of the specimen is always detected by means of an adjustable summation over different individual channels.
2. A simple digitizing of the summation channels is made possible by the summation over the individual channels because of the higher signal level.

This method should be usable in image-generating and analytic microscope systems. The microscope systems are image-generating systems such as laser scanning microscopes for three-dimensional examination of biological preparations with an optical spatial resolution of up to 200 nm, nearfield scanning microscopes for high-resolution examination of surfaces with a resolution of up to 10 nm, fluorescence correlation microscopes for quantitative determination of molecular concentrations and for measuring molecular diffusions. Also included are methods based on fluorescence detection for screening dyes.

In all of the systems mentioned above, fluorescent dyes are used for specific labeling of the preparations. The objectives mentioned above are achieved by methods and arrangements according to the invention. In accordance with the invention, a method for the optical acquisition of characteristic quantities of an illuminated specimen, wherein a signal that is backscattered, reflected and/or fluoresced and/or transmitted from the specimen comprises the steps of detecting the signal by a spatially resolving detector in a plurality of channels in that the radiation coming from the specimen is imaged on the detector so as to be spectrally split and combining detection channels so that the quantity of measurements that are read out and further processed is less than the number of detection channels.

DESCRIPTION OF THE PREFERRED EMBODIMENTS

Figure 4:
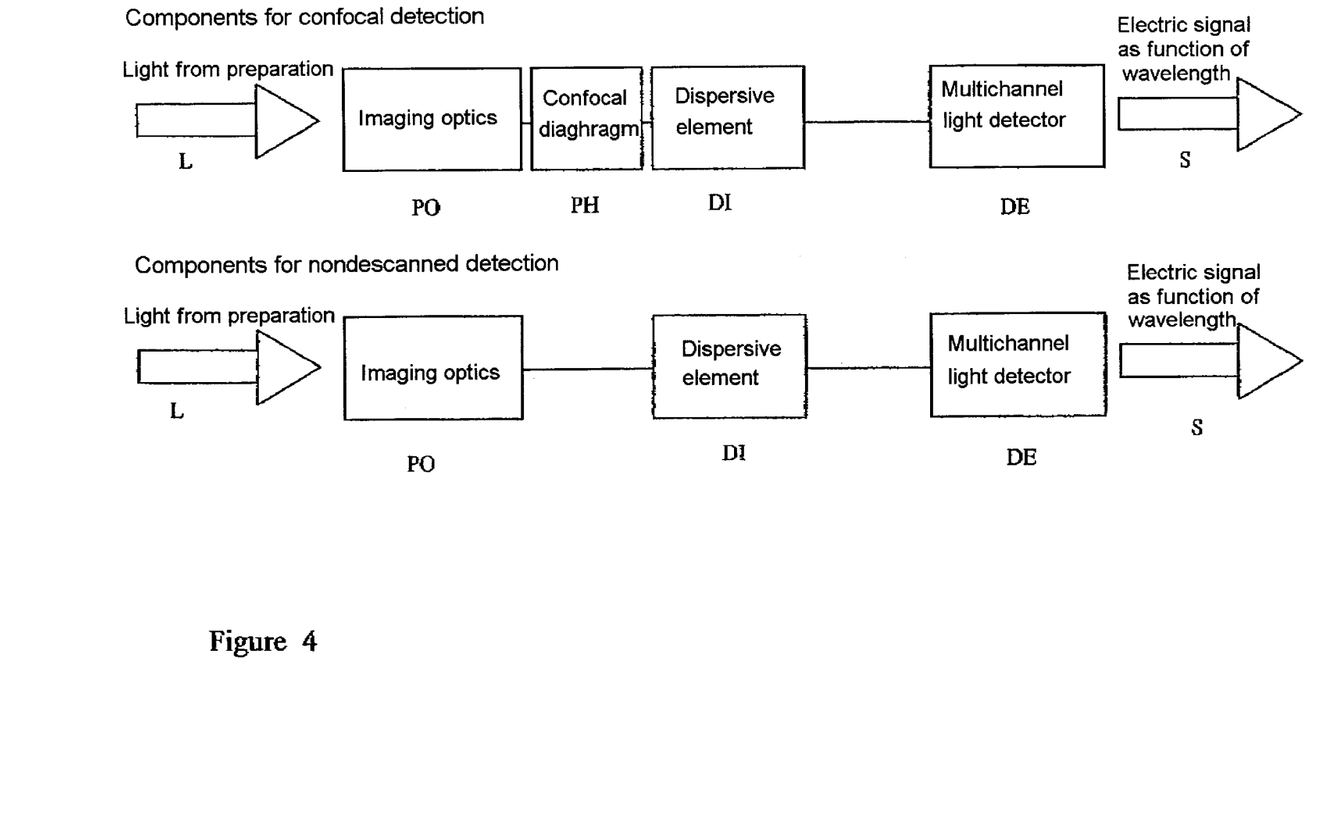
FIG. 4 shows a block diagram of a detector limit in accordance with the invention.

The method according to the invention is based on a spectrally split detection of fluorescence in which there is a summing over different spectral components. For this purpose, the emission light is split from the excitation light in the scan module or in the microscope (with multiphoton absorption) by means of an element for separating the excitation radiation from the detected radiation, such as the main color splitter (MDB) or an AOTF according to 7346DE or 7323DE. With transmitted-light arrangements, this type of element can also be entirely omitted. A block diagram of the detector unit to be described is shown in FIG. 4. With confocal detection, the light L from the specimen is focused through a diaphragm (pinhole) PH by means of imaging optics PO, so that fluorescence occurring outside of the focus is suppressed. In nondescanned detection, the diaphragm is omitted. The light is now divided into its spectral components by means of an angle-dispersive element DI. The angle-dispersive elements can be prisms, gratings and, e.g., acousto-optic elements. The light which is split into its spectral components by the dispersive element is subsequently imaged on a line detector DE. This line detector DE measures the emission signal as a function of wavelength and converts it into electrical signals. By means of a binning process, according to the invention, which will be described more fully in the following, a connection of individual channels, i.e., a summation over individual channels of the line detector, is carried out. In addition, a line filter for suppressing the excitation wavelengths can be arranged in front of the detection unit.

Figure 5:
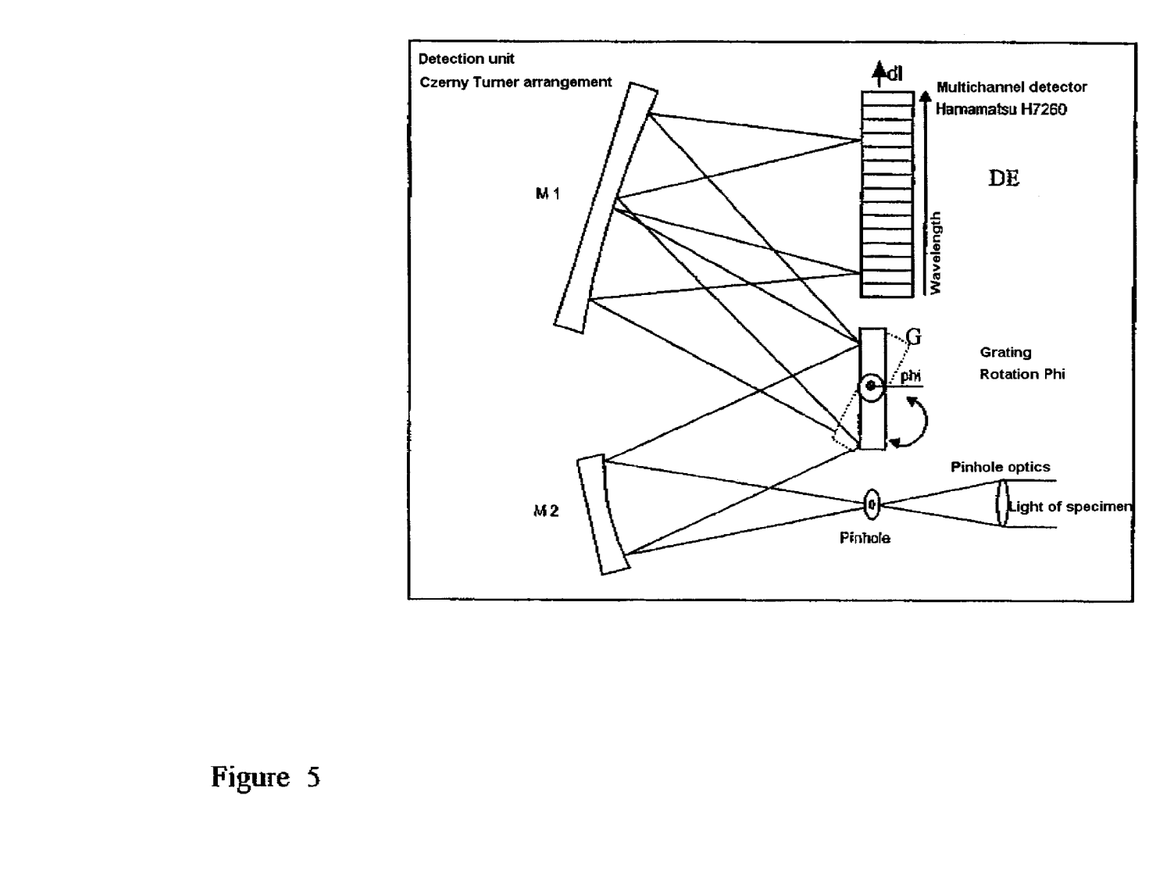
FIG. 5 shows a possible embodiment form of the optical beam path of the detector unit shown in the block diagram of FIG. 4.

FIG. 5 shows a possible embodiment form of the optical beam path of the detector unit shown in the block diagram in FIG. 4. The construction is essentially a Czerny Turner construction. In confocal detection, the light L of the specimen is focused through the confocal diaphragm PH by the pinhole optics PO. With nondescanned detection in case of multiphoton absorption, this diaphragm can be omitted. The first imaging mirror M2 collimates the fluorescent light. Subsequently, the light strikes a line grating G, for example, a grating with a line number of 651 lines per mm. The grating bends the light in different directions corresponding to its wavelength. The second imaging mirror M1 focuses the individual spectrally split wavelength components on the corresponding channels of the line detector DE. The use of a secondary electron multiplier array by Hamamatsu H7260 is especially advantageous. The detector has 32 channels and high sensitivity. The free spectral region of the embodiment form described above is approximately 350 nm. In this arrangement, the free spectral region is uniformly distributed to the 32 channels of the line detector resulting in an optical resolution of approximately 10 nm. Using the unit in an image-generating system is advantageous because the signal per detection channel is still relatively large due to the relatively broad detected spectral band. A shift of the fluorescence spectrum can be carried out, for example, by rotating the grating, rotating M1, M2 by angle phi and/or by a displacement of the line receiver in the direction of the wavelength split by dl (see Figure).

In the optical arrangements shown above, the spectral resolution is determined by the quantity of individual channels. In the embodiment forms described above, each individual channel detects a spectral band of the emission spectrum with a spectral width of approximately 10 nm. When not all of the individual channels of the detector can be read out simultaneously, a sequential readout of the individual channels (multiplexing) is carried out according to the prior art.

According to the invention, summation is carried out over individual channels with different patterns or models.

Figure 6:
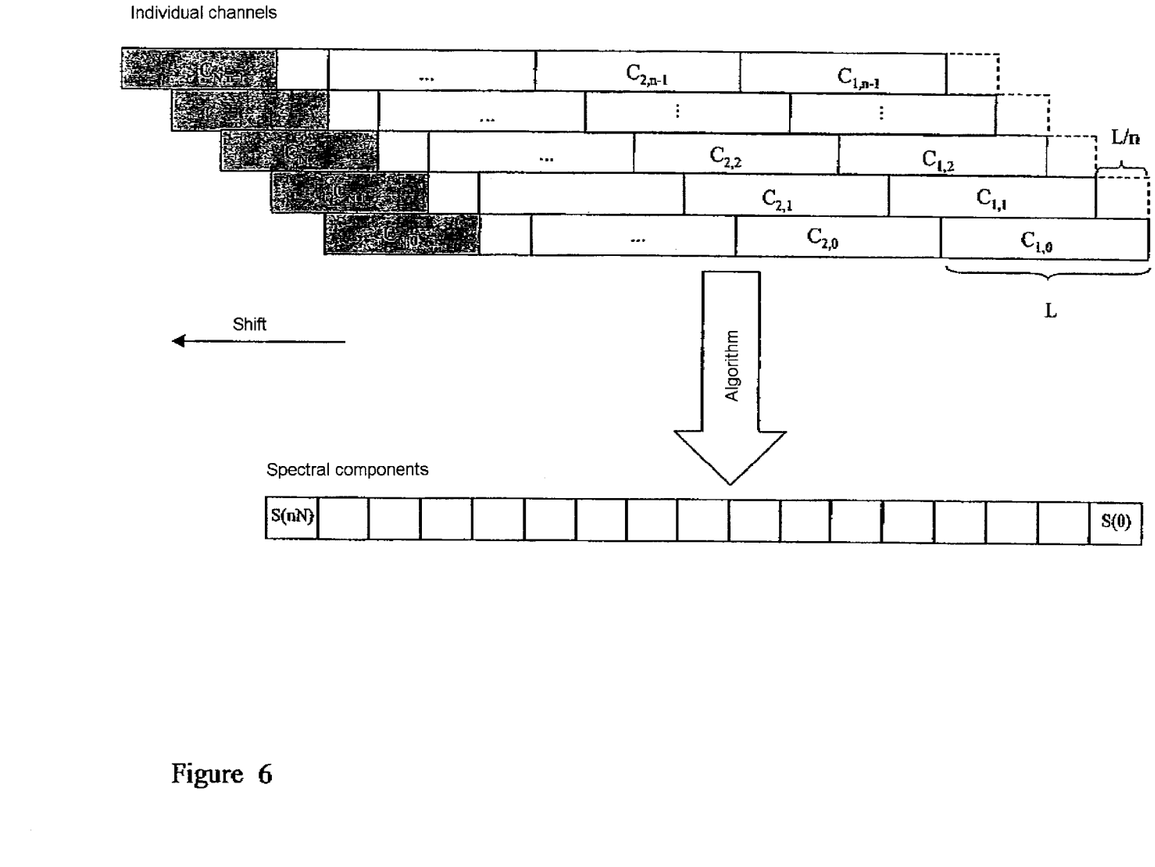
FIG. 6 represents schematically the different individual channels of the line detector, each in a line, to which N individual signals C correspond.

When eight channels can be read out simultaneously, for example, a summation is carried out over four channels in each instance, wherein the 32 channel detectors described above are used. The total N=32 channels are then read out in n=4 steps, the summation window being shifted in each instance by an individual channel (L/n=4/4=1). FIG. 6 shows schematically the different individual channels of the line detector, each in a line, to which N individual signals C correspond.

The measured signals of the individual channels are designated by $c_{kj}$ (shown as blocks in FIG. 6), where k=1 . . . N is the channel number and j=0 . . . n−1 are the multiples of the shift L/n. If the signal does not drop at the edge of the detector, the last individual channel of the detector can be covered (cut out), shown in gray in FIG. 6, in such a way that only a width of L/n is available for measurement. This is necessary for preventing artifacts when calculating.

For calculating N times n spectral values $S_m$, sums of individual channels are subtracted according to the following algorithm:

$$S_1 = c'_{1,0} = \sum_{i=1}^{N} c_{i,0} - \sum_{i=1}^{N-1} c_{i,1}$$

$$S_2 = c'_{1,1} = \sum_{i=1}^{N} c_{i,1} - \sum_{i=1}^{N-1} c_{i,2}$$

$$\vdots$$

$$S_{n-1} = c'_{1,n-2} = \sum_{i=1}^{N} c_{i,n-2} - \sum_{i=1}^{N-1} c_{i,n-1}$$

$$S_n = c'_{1,n-1} = \sum_{i=1}^{N-1} c_{i,n-1} - \sum_{i=2}^{N} c_{i,0} - \sum_{m=1}^{n-2} c_{N,m}$$

$$\vdots$$

$$S_{k \cdot n+1} = c'_{k,0} = \sum_{i=k}^{N} c_{i,0} - \sum_{i=k}^{N-1} c_{i,1}$$

$$S_{k \cdot n+2} = c'_{k,1} = \sum_{i=k}^{N} c_{i,1} - \sum_{i=k}^{N-1} c_{i,2}$$

$$\vdots$$

$$S_{k \cdot n+j+1} = c'_{k,j} = \sum_{i=k}^{N} c_{i,j} - \sum_{i=k}^{N-1} c_{i,j+1}$$

$$\vdots$$

$$S_{(k+1) \cdot n-1} = c'_{k,n-2} = \sum_{i=k}^{N} c_{i,n-2} - \sum_{i=k}^{N-1} c_{i,n-1}$$

-continued $$S_{(k+1)\cdot n} = c'_{k,n-1} = \sum_{i=k}^{N-1} c_{i,n-1} - \sum_{i=k+1}^{N-1} c_{i,0} - \sum_{m=i}^{n-2} c_{N,m}$$

$$\vdots$$

$$S_{N\cdot n-n} = C'_{N,0} = C_{N,0}$$

$$S_{N\cdot n-n+1} = C'_{N,1} = C_{N,1}$$

$$\vdots$$

$$S_{N\cdot n} = C'_{N,n-1} = C_{N,n-1}$$

The spectral values S (intermediate values) calculated in this way can subsequently be represented graphically on the displayed image, e.g., during a spectral scan.

Figure 7:
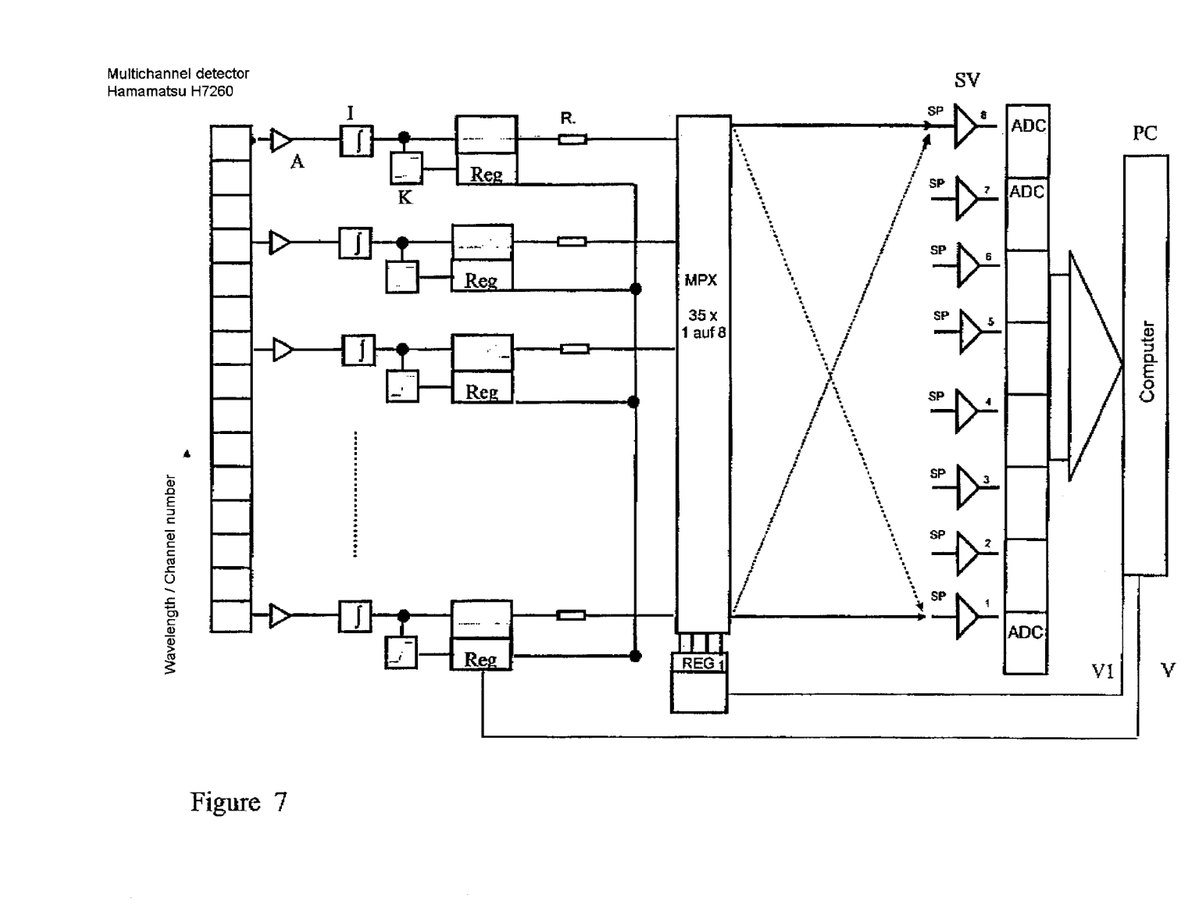
FIG. 7 schematically shows the summation over different individual channels and, accordingly, the measurement of $c_{kj}$.

FIG. 7 schematically shows the summation over different individual channels and, accordingly, the measurement of $c_{kj}$. The signals of the individual channels are transformed into voltage signals by an amplifier A. The individual voltage signals are subsequently integrated in an integrator I during the pixel dwell time. The integrator is followed by a comparator K which compares the integrated signals to a reference signal. In the event that the integrated signal was smaller than the comparator threshold, no fluorescence signal, or a fluorescence signal that is too small, would be measured in the corresponding individual channel. In such cases, the signal of the individual channel will not be further processed, since this channel only contributes a noise component to the total signal. In this case, the comparator actuates a switch SR via SR and the individual channel is cut out for the pixel that has just been measured. Accordingly, by means of the comparators in combination with the switches, the relevant spectral region is selected automatically for the image point that has just been measured.

The integrated voltage signal of the individual channels can subsequently be switched by a demultiplexer MPX connected with the switch register SR to different summing points by the register Reg1. FIG. 7 shows eight different summing points SP. The register Reg1 is controlled by the computer through a control line V1. The summation pattern or model can be controlled in a pixel-exact manner, i.e., within a time period of several $\mu$s.

Each summing point SP forms a part of the summing amplifier SV which carries out the summation of the selected individual channels. FIG. 7 shows a total of eight summing amplifiers SV. The sum signals $c_{kj}$ are subsequently converted into digital signals by an analog-to-digital converter and are further processed by the computer or DSP. The summing amplifiers SV can also be operated with a variable nonlinear characteristic.

In the arrangement described above, an integrator circuit was used for detecting the individual channel signals. However, a photon count can also take place in the individual channels, without any limitation implied.

A change in the summation pattern by V1 can be carried out imagewise after the recording or during the scanning of an image point or image line or image column. Requirements with regard to the switching speed of the MPX depend on the type of adjustment. For example, when adjustment is carried out by image point, the scan must be carried out within the integration period for this image point (that is, in several microseconds). When the adjustment is carried out by image, the scan must be carried out within several microseconds to seconds. The calculation of the signals of the individual channels is carried out with the algorithm described above using $c_{kj}$.

In the two arrangements described above, an integrator circuit was preferably used for detecting the individual channel signals. However, without implying any limitation, a photon count can also be carried out in the individual channels and the photon numbers can be added up.

In an advantageous manner, according to the invention, the detected wavelength distribution ($\lambda$-stack) is correlated imagewise in storage to the respective image point coordinate x, y or z and/or an additional time correlation is carried out with measured time-variable sequences.

While the foregoing description and drawings represent the present invention, it will be obvious to those skilled in the art that various changes may be made therein without departing from the true spirit and scope of the present invention.

What is claimed is:

1. A method for the optical acquisition of characteristic quantities of an illuminated specimen, wherein a signal is backscattered, reflected, fluoresced or transmitted from the specimen, comprising the steps of:

detecting the signal by a spatially resolving detector in a plurality of channels in that the radiation coming from the specimen is imaged on the detector so as to be spectrally split; and electronically combining detection channels so that the quantity of measurements that are read out and further processed is less than the number of detection channels.

2. The method according to claim 1, wherein the combining is a summation.

3. The method according to claim 1, wherein a shifting of the combined measurements is carried out or the number of combined detector channels is changed.

4. The method according to claim 1, wherein shifting takes place by at least one detector channel.

5. The method according to claim 1, wherein the magnitude of shifting of the detection channels is variable.

6. The method according to claim 1, wherein intermediate values are determined from read out measurements by an algorithm for the purpose of an efficient readout of a detector line.

7. The method according to claim 1, wherein a shift of the summation pattern along a line detector is carried out by a multiplexer.

8. The method according to claim 1, wherein a spectrally resolved measurement of spectra is carried out by a dispersive element preceding the detector.

9. The method according to claim 8, wherein the dispersive element is swivelable about at least one axis.

10. The method according to claim 1, wherein the spectrally split radiation is shifted relative to the detector.

11. The method according to claim 1, wherein, with a dispersive element remaining stationary in at least one of its swiveling axes, a spectrally changing effect of the swiveling in this axis is carried out by a scan unit or by displacement of the detector.

12. The method according to claim 1, wherein the detected wavelength distribution is correlated imagewise in storage to the respective image point coordinate x, y or z or an additional time correlation is carried out with measured time-variable sequences.

* * * * *